United States Patent
Stefanchik et al.

[19]

[11] Patent Number: 6,036,700
[45] Date of Patent: Mar. 14, 2000

[54] SURGICAL ANASTOMOSIS INSTRUMENT

[75] Inventors: David Stefanchik, Mason; John L. Stammen, Cincinnati, both of Ohio

[73] Assignee: Ethicon Endo-Surgery, Inc., Cincinnati, Ohio

[21] Appl. No.: 09/115,067

[22] Filed: Jul. 14, 1998

[51] Int. Cl.[7] .................................................. A61B 17/04
[52] U.S. Cl. ........................ 606/144; 606/139; 606/148
[58] Field of Search .................................. 606/144, 145, 606/146, 147, 139, 148

[56] References Cited

U.S. PATENT DOCUMENTS

| | | | |
|---|---|---|---|
| 3,019,789 | 2/1962 | Whitehill | 128/305 |
| 4,915,107 | 4/1990 | Rebuffat | 606/144 |
| 5,188,636 | 2/1993 | Fedotov | 606/144 |
| 5,411,481 | 5/1995 | Allen | 606/144 |
| 5,545,148 | 8/1996 | Wurster | 604/223 |
| 5,571,090 | 11/1996 | Sherts | 606/144 |

*Primary Examiner*—Gary Jackson
*Attorney, Agent, or Firm*—Dean Garner

[57] ABSTRACT

A surgical device and method is described for facilitating the anastomosis of two hollow organs. The surgical device has two arms for holding one of the hollow organs, each arm having a distal end, a proximal end, and a longitudinal axis extending therebetween. Each arm also includes a holding surface. The surgical device also has a means for moving the two arms near to each other and away from each other, and a means for holding the two arms near to each other. The surgical device further includes a prong having a proximal end attached to the surgical device, and a distal end of the prong for entering a hole of a hollow organ. The prong is interposed between the two arms such that when the two arms are moved near to each other, the prong and hollow organ are held between the holding surfaces of the arms, with the longitudinal axis of the prong parallel to the longitudinal axes of the two arms.

17 Claims, 10 Drawing Sheets

SURGICAL ANASTOMOSIS INSTRUMENT

FIELD OF THE INVENTION

The present invention relates, in general, to devices and methods which facilitate the anastomosis of hollow organs of the body. More particularly, it relates to vascular anastomosis devices incorporating sutures for joining a graft blood vessel to the side wall of a target blood vessel such as the aorta or coronary artery.

BACKGROUND OF THE INVENTION

Anastomosis, the surgical formation of a passage between two normally distinct organs or spaces, is a critical part of many surgical procedures. This is particularly true for coronary artery bypass graft (CABG) procedures in which one or more graft vessels are joined to coronary arteries. The distal end of the graft vessel is typically joined to the coronary artery distal to the stenosed or blocked portion of that artery, in order to improve the blood supply to the myocardium. The graft vessels normally used include the saphenous vein of the leg and the radial artery of the arm. After the graft vessels are harvested, they are cut to the correct length, and then joined on their proximal ends to a blood supply vessel, usually to the aorta. Thereafter, the distal end of the graft is attached to the coronary artery. In an alternative procedure, the internal mammary artery (IMA) is used as a graft vessel. In this procedure the artery is temporarily clamped, severed at a location allowing enough length to be redirected towards the heart, dissected from the chest wall and arterial side branches, and then the distal end (pedicle) is attached to the lower anterior descending coronary artery (LAD) to improve or restore blood flow to the myocardium of the heart. In this case, the anastomosis (the suture attachment) is made only at the distal end, or pedicle, of the IMA.

For the grafting procedures mentioned above, the type of vascular anastomosis used is typically referred to as an end-to-side type. That is, the open end of the graft vessel is attached to the side of the target vessel. However, other types of anastomosis are used as well. The end-to-end type of anastomosis is common for joining together larger hollow organs such as bowel, but can also be used for heart bypass procedures, especially for cases where the arterial flow is completely occluded by the stenosis in the diseased artery.

Some surgeons choose to complete all the proximal anastomoses to the aorta before commencing the distal anastomoses to the coronary arteries. In contrast, others choose to complete the distal anastomoses first. Regardless of the order, when undertaking the distal anastomoses to the coronary artery, it is important that the vessel graft be held steady and adjacent the coronary artery, with a minimum of vascular trauma and a minimum of visual and surgical obstruction by instruments in the narrow operative field.

Currently vascular anastomosis is accomplished by hand suturing with a tiny, curved needle and very fine suture filament. The suturing method, however, is very time consuming and requires several minutes per anastomosis, even for an experienced surgeon. In some cases the blood flow in the newly joined vessels may be poor, and the surgeon must remove the stitches and repeat the suturing procedure. In surgical procedures involving multiple bypass grafts, the time accumulated for doing the suturing is very substantial, putting the patient at risk and increasing the cost of the surgical procedure.

Hand suturing also requires a high level of skill and is not easily mastered by many surgeons. The preferred type of suturing method for the anastomosis of blood vessels is where the needle is passed through the wall of the first vessel (such as the coronary artery) from the inside to the outside, and then passed from the outside to the inside of the second vessel (such as the graft vessel), so that when the suture is drawn tight, the inside walls of the vessel come together, intima-to-intima. This is to insure that the vessels heal together properly with a smooth layer of endothelial cells formed on the inside of the anastomosis. A single stitch would first be done in this manner at each of the heel and toe locations of the anastomosis, and then a running stitch, or a series of interrupted stitches, would be made on each half of the anastomosis between the heel and toe locations.

It is especially difficult to suture if the anastomosis site is not easily accessed or viewed. For the standard CABG procedure, access to the heart is obtained via a median sternotomy in which the rib cage is split longitudinally on the midline of the chest, and the left and right rib cages are spread apart. Less traumatic means of access are becoming more widely used in recent years, including a cardiac procedure known as MIDCAB (Minimally Invasive Direct Coronary Artery Bypass). In one version of a MIDCAB, access to the heart is obtained by using a small, left thoracotomy (incision between the ribs on the left chest) directly above the heart. In this procedure, the surgeon's access to the heart and visibility of it are significantly reduced, and hand suturing is even more difficult than when using a median sternotomy. Other new developments in the surgical procedures have made conventional suturing even more difficult. More and more surgeons are operating on a beating heart to avoid the complications associated with using a heart lung bypass machine.

A number of devices for augmentation of the suturing techniques have been developed. These devices attempt with varying degrees of success to reduce the difficulty in repeatedly passing a needle and thread through the vascular walls. Recent examples are found in U.S. Pat. No. 5,571,090 issued to Sherts on Nov. 5, 1996 and U.S. Pat. No. 5,545,148 issued to Wurster on Aug. 13, 1996. In both Sherts and Wurster, the devices described are for facilitating the passing of the needle through the tissue. Individual stitches, however, must still be made one at a time, and therefore, the anastomosis procedure is still time consuming and tedious. This is because a significant portion of the time required for suturing together very small blood vessels is spent on properly capturing a margin of tissue to be penetrated with the needle, and then placing the needle at precisely the correct distance from the edge of the incision and from the adjacent stitch.

Another variety of devices well known in the surgical art are known as purse string devices. They incorporate a method for holding a severed end of a tubular organ between two clamping implements and providing passages through these implements in order to guide a needle and an attached suture filament. Then several stitches can be made at once with the stitches being precisely spaced apart. The clamping surfaces of the implements contain interlocking teeth or undulations so that the tissue assumes a serpentine shape when thus clamped. The suture filament is sewn into the organ so that its lumen can be drawn closed by pulling on the ends of the suture filament. Some examples of these devices are described in U.S. Pat. No. 4,915,107 issued to Rebuffat, et al, on Apr. 10, 1990, U.S. Pat. No. 5,188,636 issued to Fedotov on Feb. 23, 1993, and U.S. Pat. No. 5,411,481 issued to Allen, et al, on May 2, 1995. These devices were described for use on large tubular organs such as bowel, and they were each intended for applying the purse string suture to the severed end of one organ. This type of suturing technique is commonly used in combination with surgical, circular staplers for the anastomosis of large hollow organs such as the small and large intestines. The purse string suture is used to draw down the lumen of the hollow organ around a shaft of the stapling instrument prior to stapling. In all of these examples for purse string devices, the tissue wall of the hollow organ to be sutured is held by the device so as to have a serpentine shape in the longitudinal direction. A straight needle is then passed manually through the "peaks" of the indulations.

Another device which is somewhat similar to the purse string devices is described in U.S. Pat. No. 3,019,789 issued to Whitehill, et al, on Jun. 30, 1958, and is described for use in the side-to-side anastomosis of blood vessels. The device described requires that an incision be made in each of the blood vessels to be joined. The device has two, slender clamping implements with mating, serpentine, clamping surfaces. Each implement is inserted into the incision of the respective blood vessel, then the implements are brought together and locked, thus holding the vessels side by side with the compressed vessel walls taking on the serpentine shape. Longitudinal holes in the implements are used to guide straight needles so as to join the two vessels together with the suture filaments. A longitudinal slot between the needle holes is provided so that a knife can be pushed through the length of the implements in a manner which results in the creation of a passage between the vessels. The device is then removed and the ends of the suture filaments are finally tied together. A drawback of this device is that the purse string type of stitches created in the joined vessels is not the type described earlier which is preferred by surgeons for creating an anastomosis. A further drawback is that the device is described only for use in a side-to-side anastomosis. As noted earlier, the type of anastomosis required most often for coronary artery bypass procedures is of the end-to-side type. Perhaps the most significant drawback, however, in light of the new surgical procedures being developed, is the need to put the clamping arms of the device inside the lumens of the vessels to be joined. This precludes the ability to anastomose vessels while blood flow is maintained within them, and also greatly limits the size range of vessels which can be joined together with the device.

For any surgical device used for vascular anastomosis, it is extremely important that both the graft and the target vessel not be manipulated to the extent that significant trauma to the vessels occurs. Again, this is to insure that the vessels heal together properly and a smooth passage between them is created. Current methods of vascular anastomosis of a graft to the coronary artery require that blood flow be temporarily stopped using some kind of clamping device on each vessel proximal to the anastomosis site. These clamping devices can risk injury to the artery, thus comprising the long term viability of the vessel to maintain blood flow.

Because of the aforementioned considerations, there is a need to provide a surgical device for facilitating the placement of sutures for the side-to-side or end-to-side types of anastomosis of very small hollow organs such as blood vessels. There is a need that the device require minimal manipulation of the blood vessels and that the resulting anastomosis be non-leaking. There is a need that such a surgical device not introduce structures within the blood vessels which may unduly damage the delicate interior lining of the vessels, and that the inside, endothelial lining of the vessels be permitted to heal rapidly. Furthermore, there is a need for the surgical device to facilitate the anastomosis of the blood vessels while blood flow through the target vessel is maintained. Finally, there is a need that the device be adaptable to use in traditional, open cardiac procedures (CABG) as well as in less invasive procedures such as MIDCAB.

SUMMARY OF THE INVENTION

The present invention is a surgical device which can be used to facilitate the anastomosis of two hollow organs, particularly two blood vessels, in the end-to-side or side-to-side variations. In the following descriptions, the present invention is described in use with blood vessels, or simply vessels. A pair of the surgical devices are used in combination to join the vessels, using a surgical needle with a suture filament attached thereto.

The present invention has two arms for holding one of the hollow organs, each arm having a distal end, a proximal end, and a longitudinal axis extending therebetween. Each of the arms also has a holding surface and a working surface. A means is provided for moving the arms near to each other or apart from each other. The longitudinal axes of the two arms are essentially parallel when the two arms are near to each other. The present invention also provides a means for holding the two arms near to each other.

The surgical device of the present invention includes a prong having a distal end and a proximal end with a longitudinal axis extending therebetween. The proximal end is attached to the surgical device. The distal end is for entering a hole in the hollow organ. The prong is interposed between the two arms such that when the arms are moved together, the prong and the hollow organ are held between the holding surfaces of the arms. The longitudinal axis of the prong is essentially parallel to the longitudinal axes of the arms when the arms are near to each other. In a preferred embodiment, a gripping means including a plurality of teeth is provided on the holding surfaces of the two arms.

The surgical device further includes a means for creating a passageway in the hollow organ held between the arms. In the preferred embodiment, this means is a surgical scalpel used along the working surfaces of the two arms. This passage can be created while flow (of blood, etc.) is maintained in the hollow organ.

The present invention also includes a plurality of needle guides on the working surface of each arm for the accurate placement of sutures into the peripheral edge of the passage of the hollow organ. By using two of the surgical devices of the present invention, the anastomosis of two hollow organs using a needle and a suture filament is facilitated. The present invention may be adapted for use with a variety of surgical suturing techniques.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

The drawings are not necessarily to scale.

DETAILED DESCRIPTION OF THE INVENTION

Figure 1:
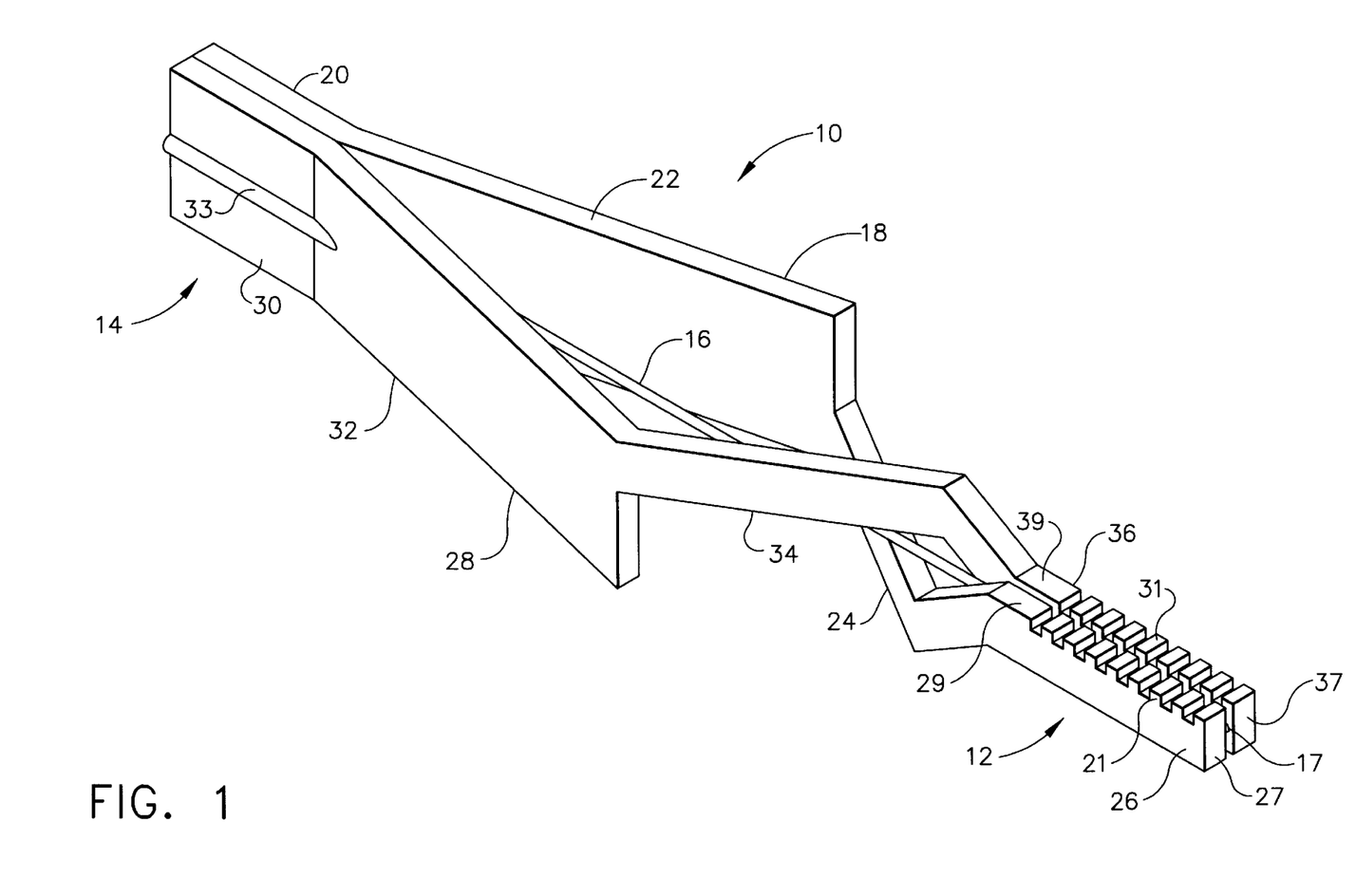
FIG. 1 is an isometric view of a first surgical device of the present invention.

A preferred embodiment of a first surgical device 10 of the present invention is shown in FIG. 1. As will be described, a second, identical surgical device 110 (see FIG. 10) is used with the first surgical device 10 in order to facilitate the anastomosis of two blood vessels, sometimes referred to simply as vessels.

As shown in FIG. 1, the surgical device 10 resembles a surgical (or "bulldog") clamp well-known in the surgical art for the occlusion of blood vessels. Surgical device 10 is about 50 mm long, although the length may vary, and comprises a first arm 18, a second arm 28, and a center prong 16 running the entire length of the surgical device 10 and along the longitudinal axis. The two arms, 18 and 28, are sometimes referred to together as a handle. First arm 18 is an elongated member made of a metal such as stainless steel or a rigid, medical grade plastic. Starting from the proximal end, the first arm 18 comprises a proximal portion 20, a wide portion 22 angled outwardly from the proximal portion, a narrow portion 24 angled inwardly from the wide portion 22, and a distal portion 26 angled outwardly from the narrow portion 24. On a working surface 29 of the distal portion 26 of first arm 18 is a plurality of first flutes 21, also referred to as guides, spaced evenly and longitudinally from the first distal tip 27. The number of flutes 21, their geometry and spacing can vary. In this embodiment, there are eight flutes on each arm. Each flute is approximately 0.5 mm wide by 0.5 mm deep, and spaced 0.5 mm from the adjacent flute. The second arm 28 is similar to the first arm 18, comprising a proximal portion 30, a wide portion 32 angled outwardly from the proximal portion 30, a narrow portion 34 angled inwardly from the wide portion 32, and a distal portion 26 angled outwardly from the narrow portion 34. On a second working surface 39 on distal portion 36 of second arm 28 is a plurality of second flutes 31, identically sized and spaced as first flutes 21. The proximal portion 20 of first arm 18 is attached (by welding or other means) to the proximal portion 30 of the second arm 28, with center prong 16 sandwiched between. Creases 33 and 23 (see FIG. 4) are formed into the second arm 28 and the first arm 18, respectively, to facilitate the attachment to the center prong 16.

Figure 2:
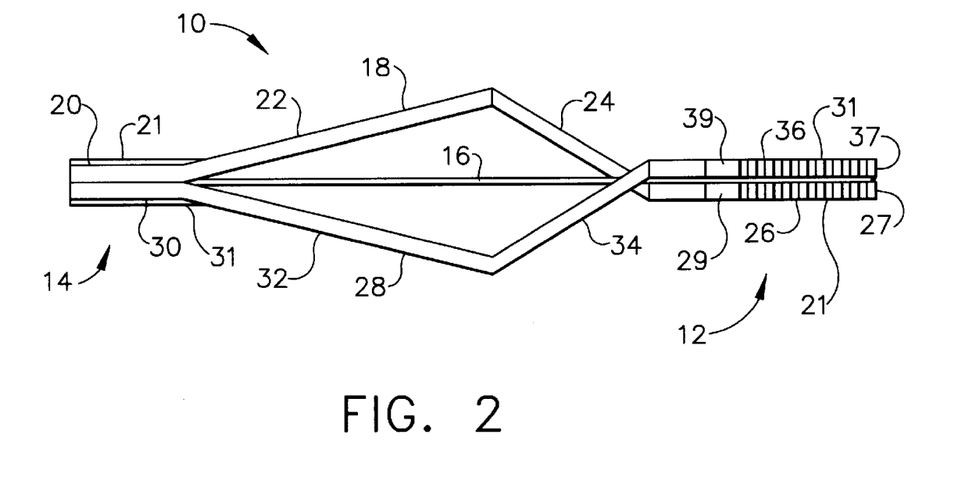
FIG. 2 is a top view of the first surgical device.

In FIGS. 1 and 2 is shown a first and a second bend, 3 and 5 respectively, located between the proximal and distal ends of the first arm 18. A first and a second bend, 2 and 4 respectively, are likewise located on the second arm 28. The narrow portions, 24 and 34, of the arms, 18 and 28, cross over each other between the first and second bends of each arm. The center prong 16 is located along the longitudinal axis and between the narrow portions. The opposing wide portions, 32 and 22, form the gripping and squeezing portion of the surgical device 10. The bending elasticity of the arms, 18 and 28, cause the opposing distal portions, 26 and 36, to be normally spring biased in a closed position. One skilled in the art will recognize that a helical coil compression spring may also be mounted between the arms, 18 and 28, proximal to the first bends, 2 and 3, in order to spring bias the distal portions, 26 and 36, into a closed position.

Figure 3:
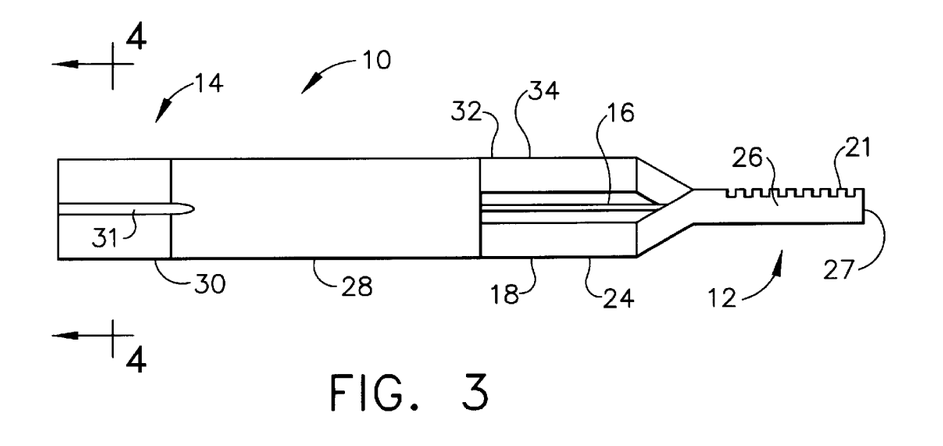
FIG. 3 is a side view of the first surgical device.
Figure 4:
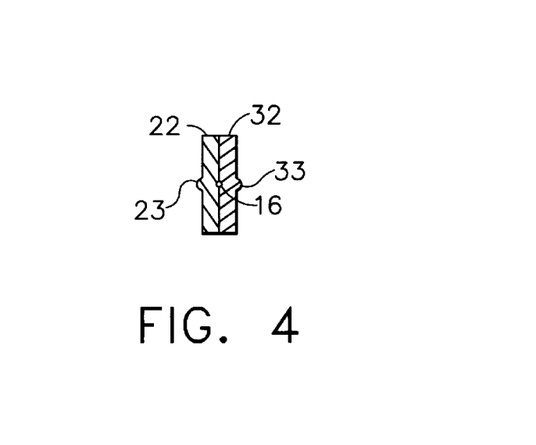
FIG. 4 is a sectional view of the first surgical device taken along line 4—4 of FIG. 3.

FIGS. 3 and 4 are additional views of the surgical device 10.

Figure 5:
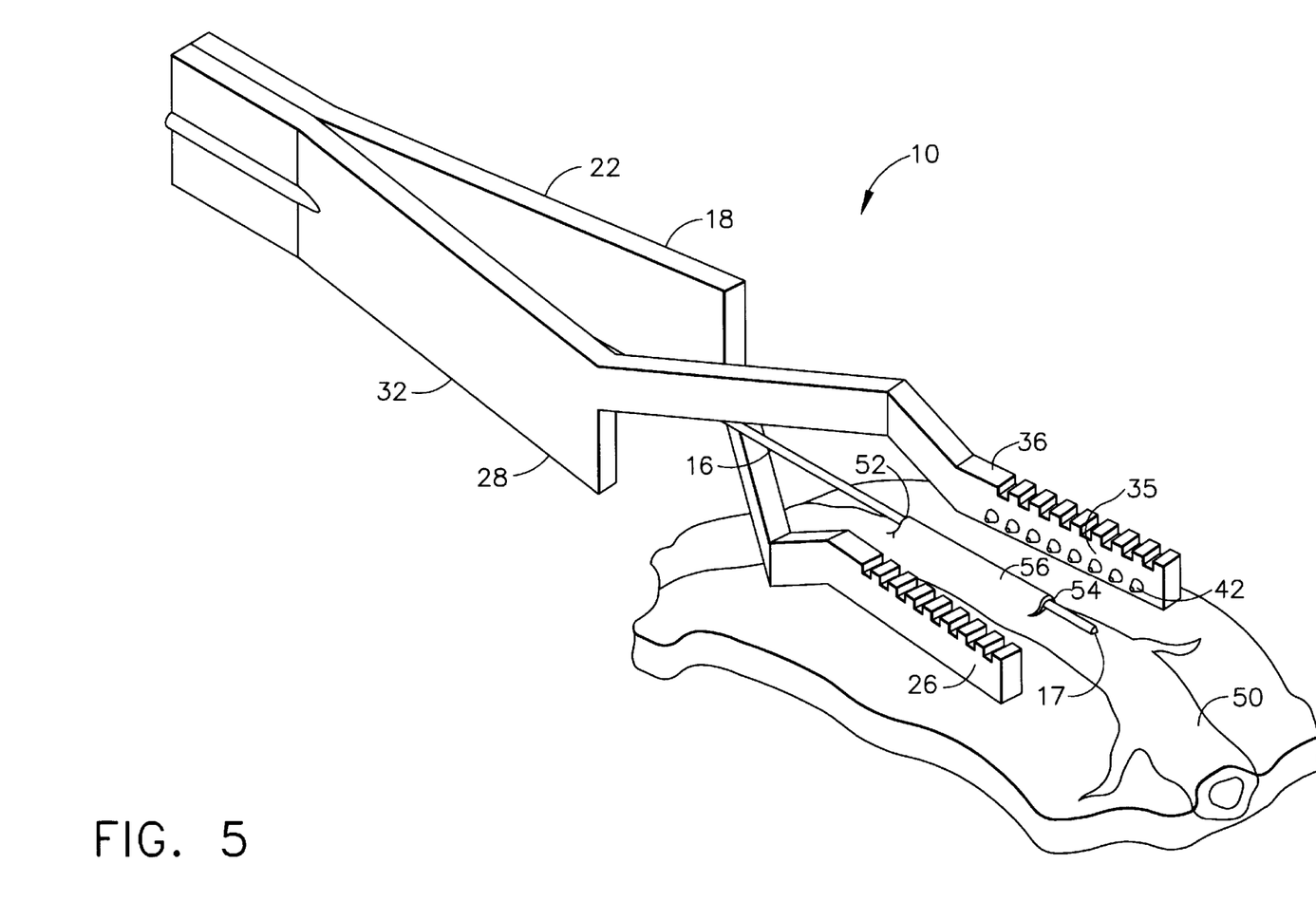
FIG. 5 is an isometric view of the first surgical device as it is being positioned on a target blood vessel such as a coronary artery.

Next described are the steps for using the preferred embodiment of the present invention for facilitating the end-to-side anastomosis of two blood vessels. In FIG. 5 the surgical device 10 is shown in an opened position. (The surgeon's hand would be squeezing together the opposing wide portions, 22 and 32, and is not shown for clarity.) In this view can be seen a plurality of teeth 42 spaced evenly in a row and extending from a holding surface 35 of distal portion 36 of second arm 28. There is an opposing plurality of teeth 44 (also referred to as projections or gripping means) extending from a holding surface 25 (see FIGS. 6 and 7) of first distal portion 26 of first arm 18. The teeth, 42 and 44, help to atraumatically hold the blood vessel between the holding surfaces, 25 and 35. In FIG. 5 can be seen how the prong tip 17 of the center prong 16 has first been inserted into a first opening 52 of blood vessel 50, and exited out a second opening 54 of the same blood vessel 50, thus forming an anastomosis portion 56. The openings, 52 and 54, can be created by using the prong tip 17 to pierce the blood vessel 50 with the assistance of a forceps to tent or support the blood vessel 50. They can also be made by first cutting into the blood vessel with a surgical scalpel or other surgical tool before inserting the prong tip 17. A combination of the two techniques could also be used. The openings, 52 and 54, are only large enough for the center prong 16 to pass through so as to maintain a seal and prohibit blood flow to escape through the interface between the center prong and the respective opening. Some oozing is generally permissible.

The length of the anastomosis portion 54 is important and should be sized approximately equal to the diameter of the graft blood vessel to which it will be attached. Also, it is not necessarily essential that the prong tip 17 exit the blood vessel 50. The prong tip 17 may be only inserted in opening 52 a distance about equal to the graft vessel diameter, and the steps to be described next for completing the anastomosis would still be the same.

Figure 6:
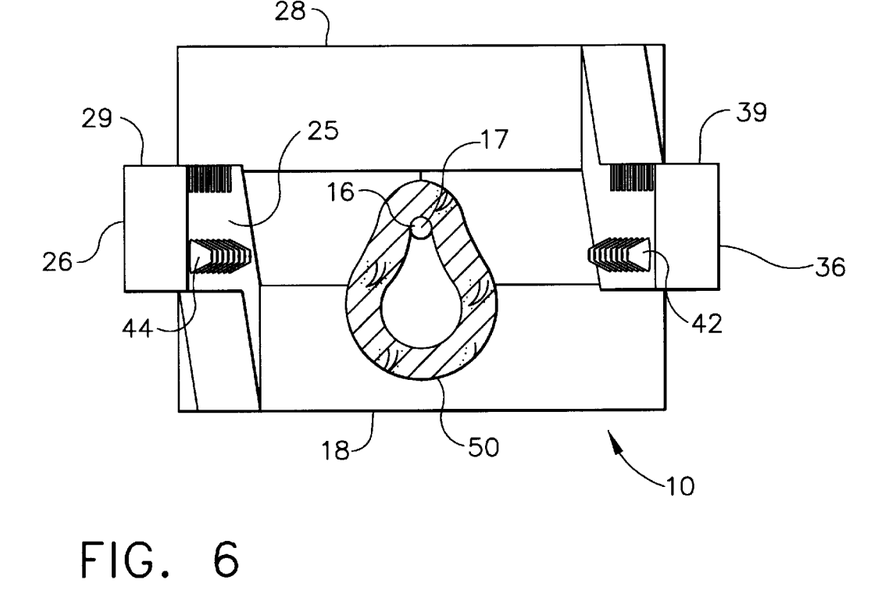
FIG. 6 is a view of the distal end of the first surgical device, with the center prong inserted in the target blood vessel and before the arms are closed onto the blood vessel.
Figure 7:
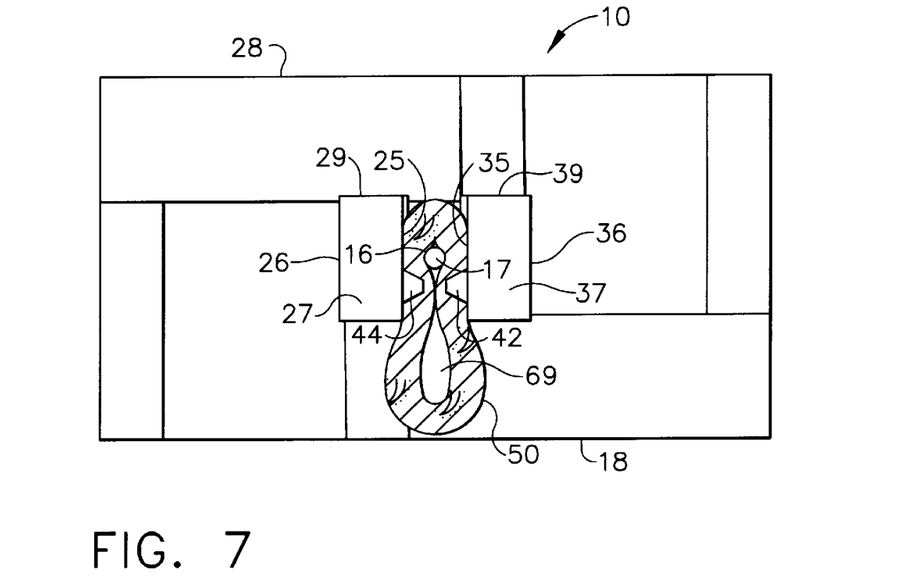
FIG. 7 is a view of the distal end of the first surgical device, with the center prong inserted into the target blood vessel and after the arms have closed onto the vessel.

FIG. 6 is an end view depicting the sectioned, target blood vessel 50 captured by the surgical device 10 as described for FIG. 5. In this view the rows of first and second teeth, 42 and 44, can be seen extending off of holding surfaces, 35 and 25 respectively. The working surfaces, 29 and 39, of arms, 18 and 28 respectively, are oriented on the top side of the surgical device 10 in this view. The prong tip 17 of center prong 16 is seen from the end view, and is used to help form the blood vessel 50 into the pear shape as shown.

In FIG. 6 the arms, 28 and 18, have been released by the surgeon to allow the distal portions, 26 and 36, to come together. Holding surfaces, 25 and 35, are shown compressing the blood vessel 50 with the center prong 16 captured between. By partially opening and closing the holding surfaces, 25 and 35, a number of times, while gently lifting on the surgical device 10, the surgeon is able to milk the walls of the blood vessel 50 over the center prong 16 until its top surface is approximately flush with the working surfaces, 29 and 39, of the surgical device 10. The teeth, 42 and 44, further serve to cusp the walls of the blood vessel 50 around the center prong 16. Blood may continue to flow through an opening 69 of blood vessel 50. As noted earlier, this is an important feature when performing surgery on a beating heart.

Figure 8:
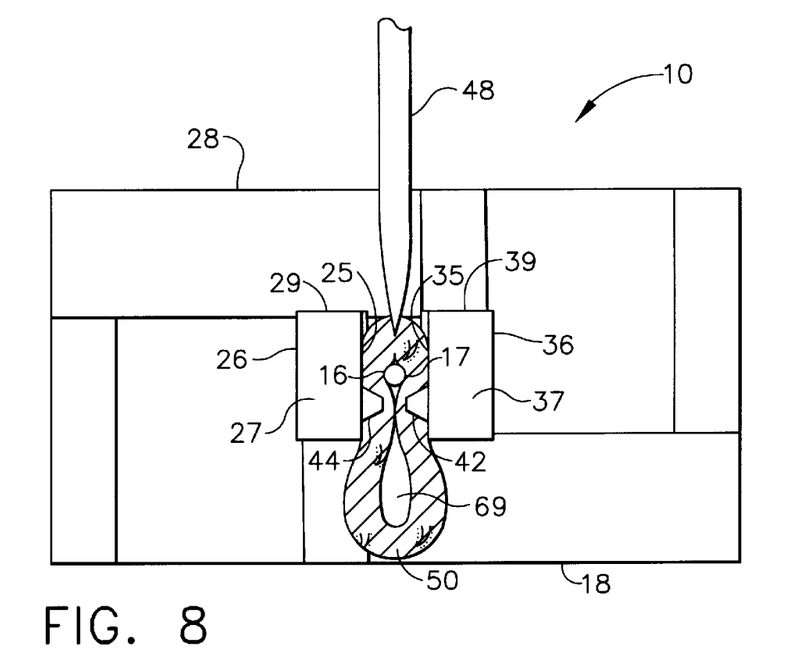
FIG. 8 is the same view as shown in FIG. 7, showing a knife being used to cut the target blood vessel between the clamping surfaces.

Now referring to FIG. 8, a surgical scalpel 48 is used to incise the portion of blood vessel 50 between the working surfaces, 29 and 39. The length of the incision is approximately equal to the diameter of the vessel to which it will be attached, and is centered longitudinally on the distal portions, 26 and 36. The center prong 16 serves as a cutting surface while the incision is made.

Figure 9:
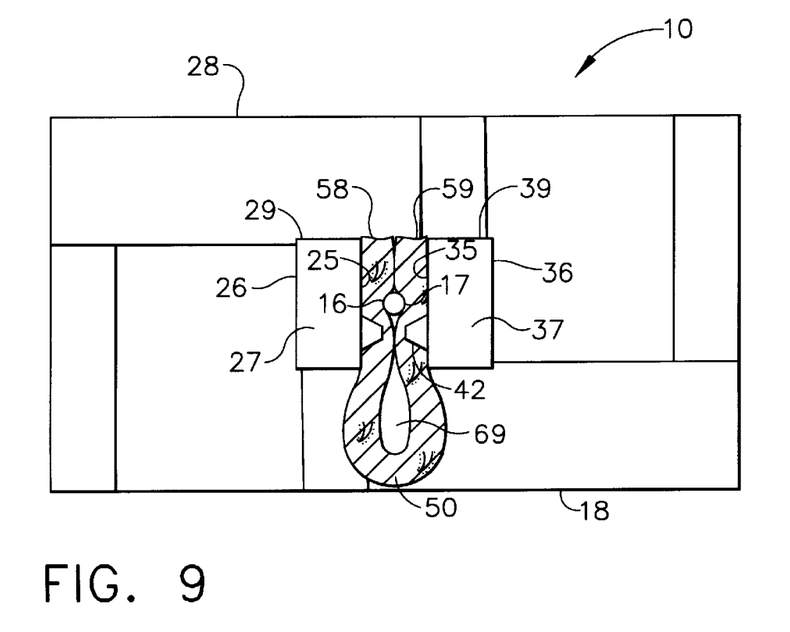
FIG. 9 is the same view as shown in FIG. 8, and showing the cut edges of the target blood vessel.

In FIG. 9, the completed incision has created a first joining edge 58 and a second joining edge 59 of blood vessel 50. Blood flow is not permitted to escape from the incised vessel due to the pressure of the holding surfaces, 25 and 35, against the vessel walls with the center prong 16 therebetween.

Figure 10:
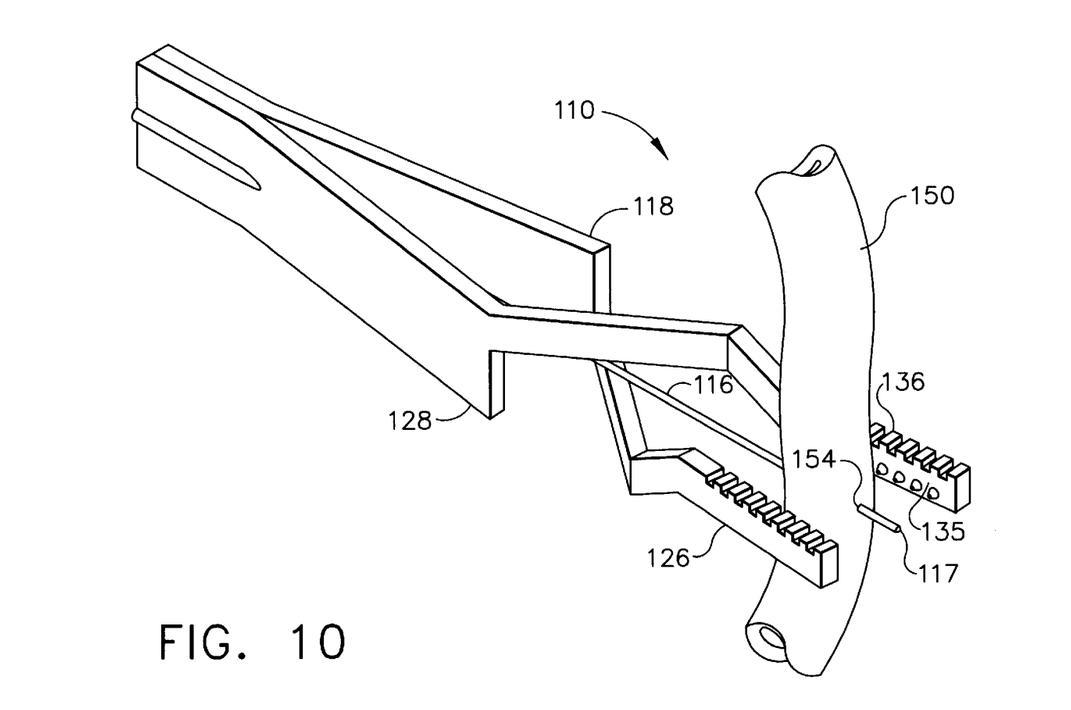
FIG. 10 is an isometric view of a second surgical device of the present invention, identical to the first, as it is applied to a graft blood vessel, and with the arms open.

A second surgical device 110 (which is identical to the first surgical device 10 already described for use on a target blood vessel 50) is shown in FIG. 10 being applied to a graft blood vessel 150. In the steps that follow, the graft blood vessel 150 is prepared for an end-to-side anastomosis to the target blood vessel 50.

In FIG. 10 the surgical device 110 is shown opened and with the center prong 116 inserted through opposite walls of blood vessel 150. (Again, the surgeon's hand is not shown for clarity.)

Figure 11:
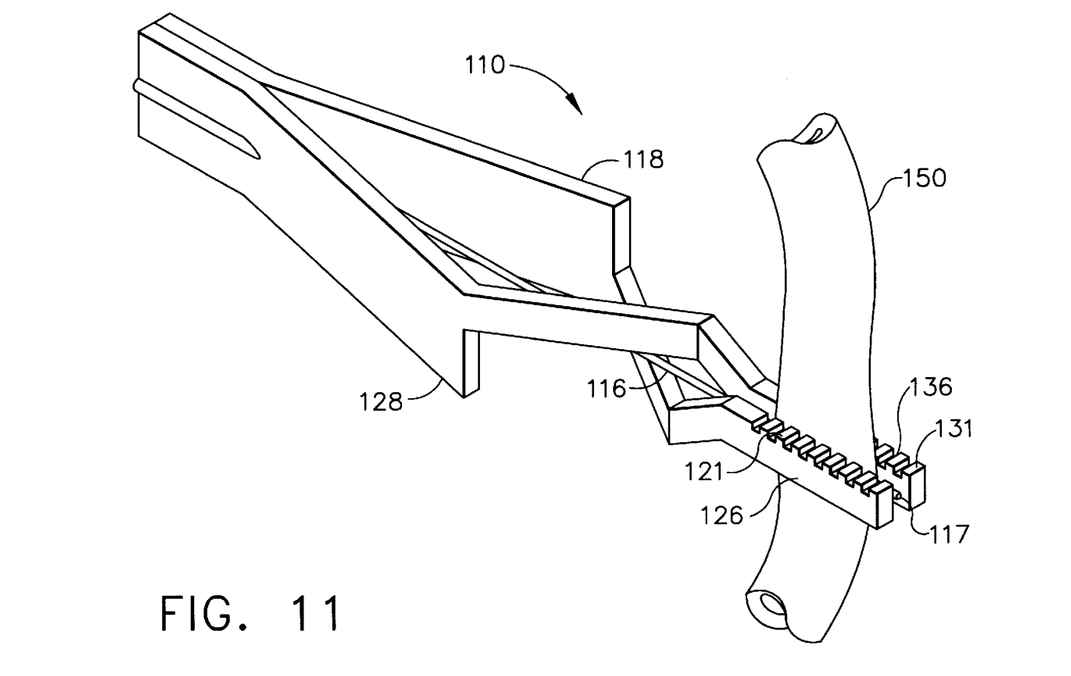
FIG. 11 is an isometric view of the second surgical device as it is applied to a graft blood vessel, and with the arms closed.

In FIG. 11 the surgical device 110 is shown clamped onto the blood vessel 150 at a location where it is desired to join the vessel to the target blood vessel 50. The blood vessel is flattened atraumatically between the distal portions, 126 and 136, and centered longitudinally along the rows of flutes, 121 and 131. It is not necessary that the longitudinal axis of the blood vessel 150 be perpendicular to the longitudinal axis of the surgical device 110. It fact, it may be desired by the surgeon for the axis of the blood vessel 150 to form a different angle to the axis of the surgical device 110 so that the eventual angle of approach of the graft vessel to the target vessel is a gradual turn to prevent "kinking" of the graft vessel, resulting in loss of blood flow to the target vessel.

Figure 12:
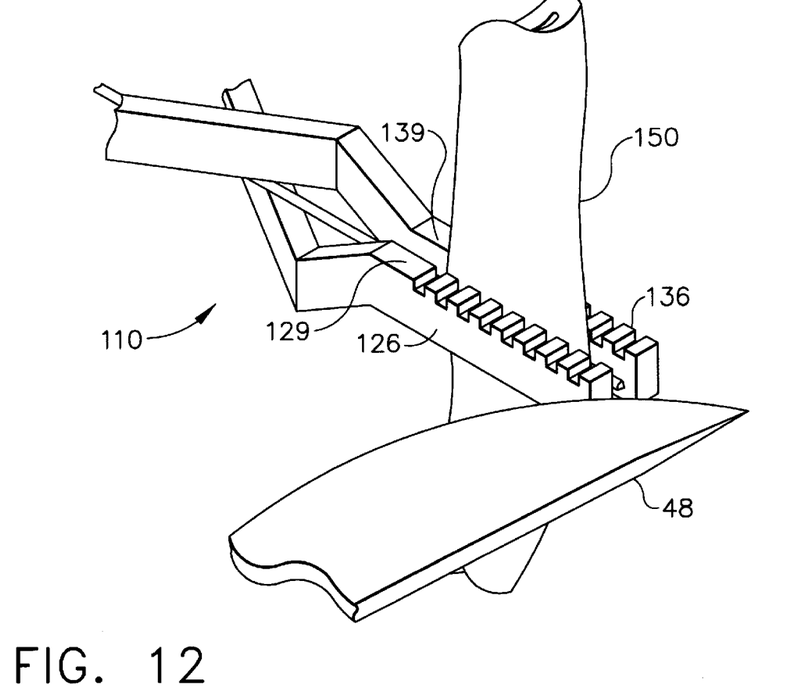
FIG. 12 is an isometric view of the second surgical device clamped onto the graft blood vessel, and while a surgical scalpel is used to cut the excess distal portion of the vessel.

FIG. 12 shows a surgical scalpel 48 being used to trim away the excess portion of the graft blood vessel 150. Working surfaces, 129 and 139, are used as a cutting guide. As in the case of the target blood vessel 50, it is not necessary to occlude the blood vessel 150 proximal to the location of the clamped surgical device 110.

Figure 13:
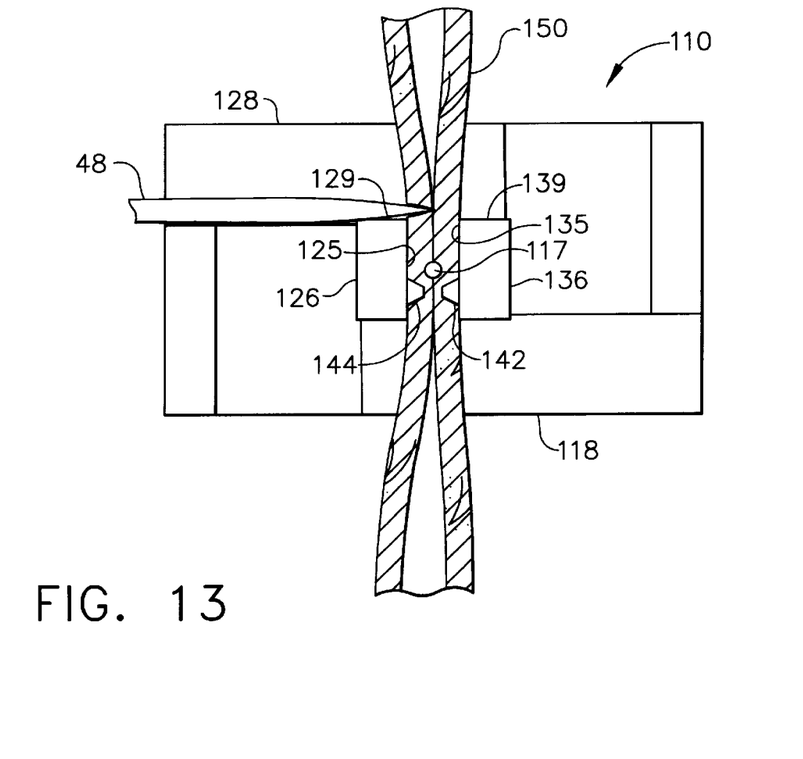
FIG. 13 is an end view of the second surgical device clamped onto the graft blood vessel, and with the surgical scalpel being used to cut the excess distal portion of the vessel.

FIG. 13 is an end view of the blood vessel 150 as it is being held by the surgical device 110 and cut by surgical scalpel 48. Teeth, 142 and 144, help hold the vessel 150 between the holding surfaces, 125 and 135.

Figure 14:
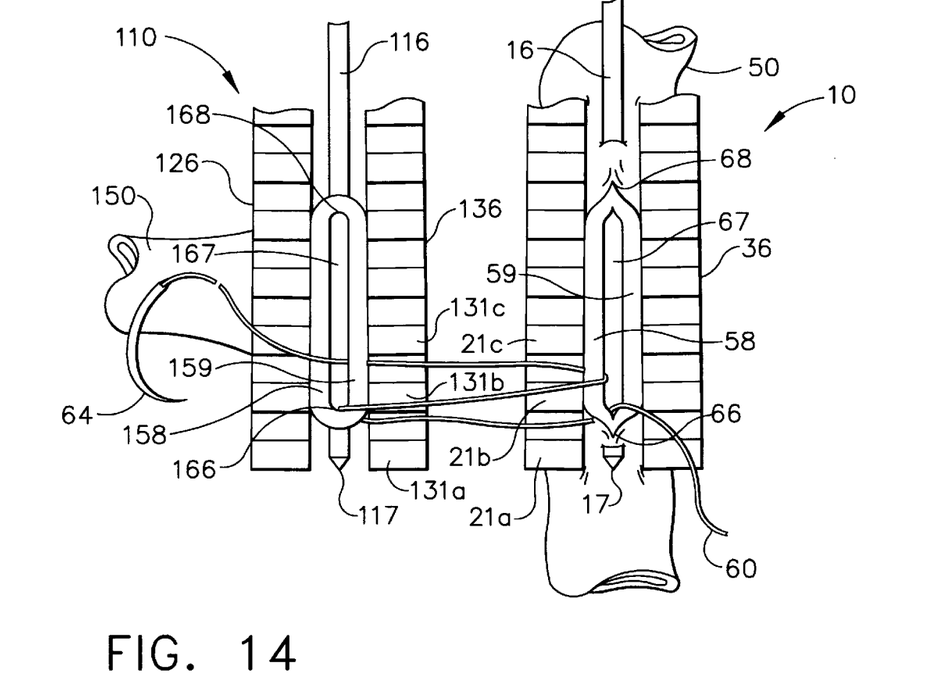
FIG. 14 is a top view of the distal portions of the first and second surgical devices clamped onto the blood vessels, and a suture filament being passed through the cut edges of the blood vessels.
Figure 15:
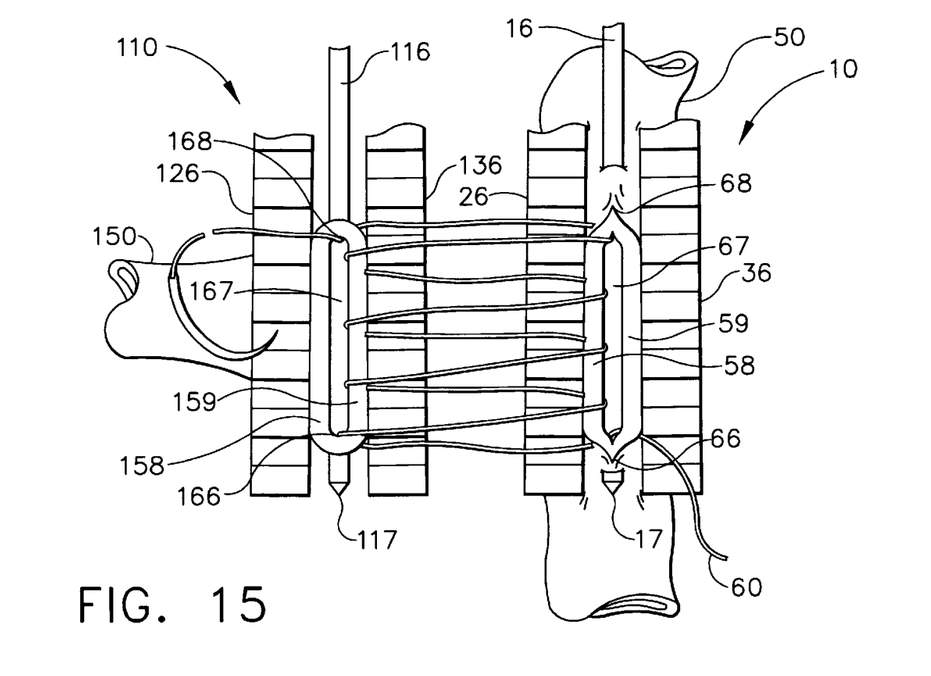
FIG. 15 is a top view of the surgical devices shown in FIG. 14, and with the inside walls of the blood vessels loosely attached by the suture filament.

Now turning to FIG. 14, the sequence for attaching the two blood vessels, 50 and 150, to each other with a passageway therebetween, using a suture filament 60, is described. Various suturing methods may be used to create the anastomosis, but what is described here incorporates a single running stitch, using a single suture filament 60 with a needle 64 attached on one end. It would also be possible, and perhaps desired by some surgeons, to use a plurality of interrupted stitches instead, or a combination of interrupted stitches and running stitches.

In FIG. 14 the surgical device 110 is shown alongside the surgical device 10, with the respective blood vessels, 150 and 50, clamped in each. Also for the vessel 50 is shown a lumen 67 having a heel 66 and a toe 68. Also shown is first and second joining edges, 58 and 59 respectively, of blood vessel 50. Similarly for blood vessel 150 is a lumen 167 having a heel 166 and a toe 168, and joining edges, 158 and 159. For the suturing method to be described, it is advantageous for the surgeon to align the individual flutes 21 of surgical device 10 with the individual flutes 131 of the surgical device 110, so that it is easy to keep track of which stitch is being made between the two vessels. Also, it is desirable to minimize the length of suture spanning between the two surgical devices, so that when the vessels are brought together by drawing the sutures, a minimal length of suture is pulled through the holes created in the vessel walls. The desired alignment of the two surgical devices may be maintained during the suturing by a number of ways, including the surgeon merely holding the surgical devices, 10 and 110, together in one hand and doing the stitching with the other. Another way for holding the two surgical devices in alignment is to lock onto the proximal portions, 20 and 30 (see FIG. 1), with a surgical clamp which in turn can be rested on the surgical retractor being used to hold open the thoracotomy incision. A person having ordinary skill in the art could also devise a holding fixture especially adapted for detachably holding the two surgical devices in alignment and adapted for CABG or MIDCAB procedures.

Still looking at FIG. 14, the suturing proceeds as follows: needle 64 is passed through the heel 66 of joining edge 58 of vessel 50, from the inside to the outside, and using the space between flutes 21a and 21b as a template or guide. The needle 64 is next passed through the heel 166 of joining edge 159 of vessel 150, from the outside to the inside, using the space between flutes 131a and 131b as a guide. Then needle 64 is passed through joining edge 58 of vessel 50, using the space between flutes 21b and 21c as a guide. These steps are repeated, progressing along the length of the joining edges, 58 and 159, until the last stitch is placed at the toes, 68 and 168, of the two vessels, 50 and 150 respectively. FIG. 14 shows the completed first half of the suturing method, with the inside joining edges, 58 and 159, loosely sutured together.

Figure 16:
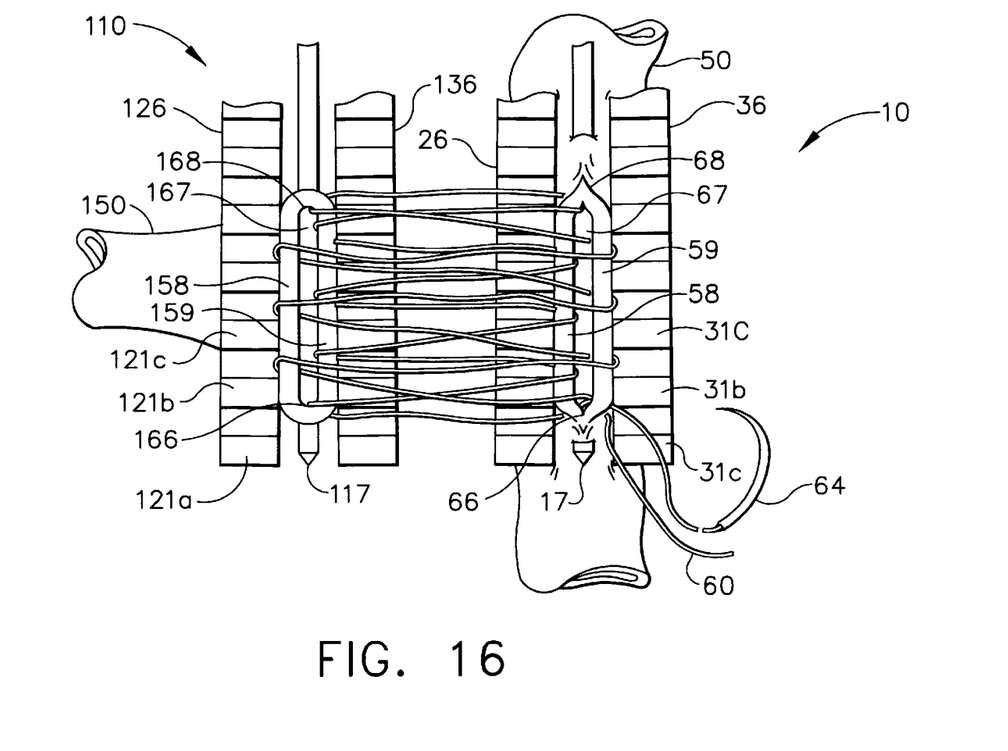
FIG. 16 is a top view of the surgical devices shown in FIGS. 14 and 15, and with the inside and outside walls of the blood vessels loosely attached by the suture filament.

In FIG. 16 can be seen how the suturing continues, now applying the stitches to the joining edges 158 and 59, starting from the toes, 168 and 68. The spaces between the flutes, 121 and 31, of surgical devices, 110 and 10 respectively, are used as guides to properly space the stitches apart, and to uniformly regulate the amount of vessel wall encompassed by each stitch (the "bite"). The last stitch is made at the toe 66 of vessel 50, alongside the first stitch. The needle 64 is trimmed from the filament 60, leaving a sufficient length to form a knot.

Figure 17:
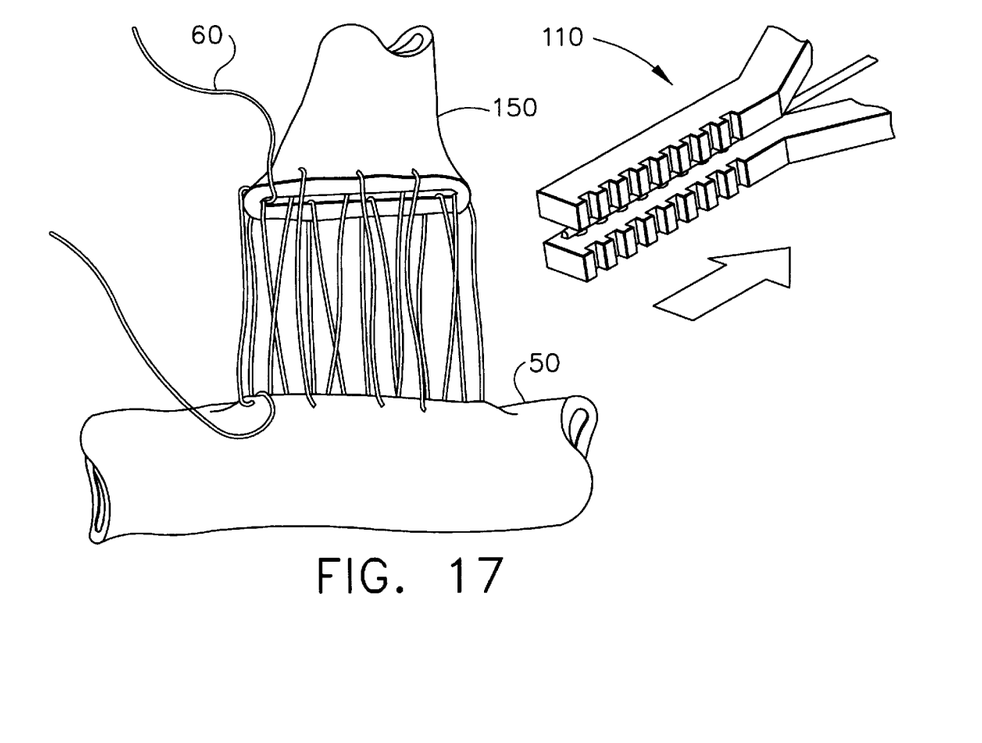
FIG. 17 is an isometric view of the graft and target blood vessels loosely attached with the suture filament, and with the first and second surgical devices removed.
Figure 18:
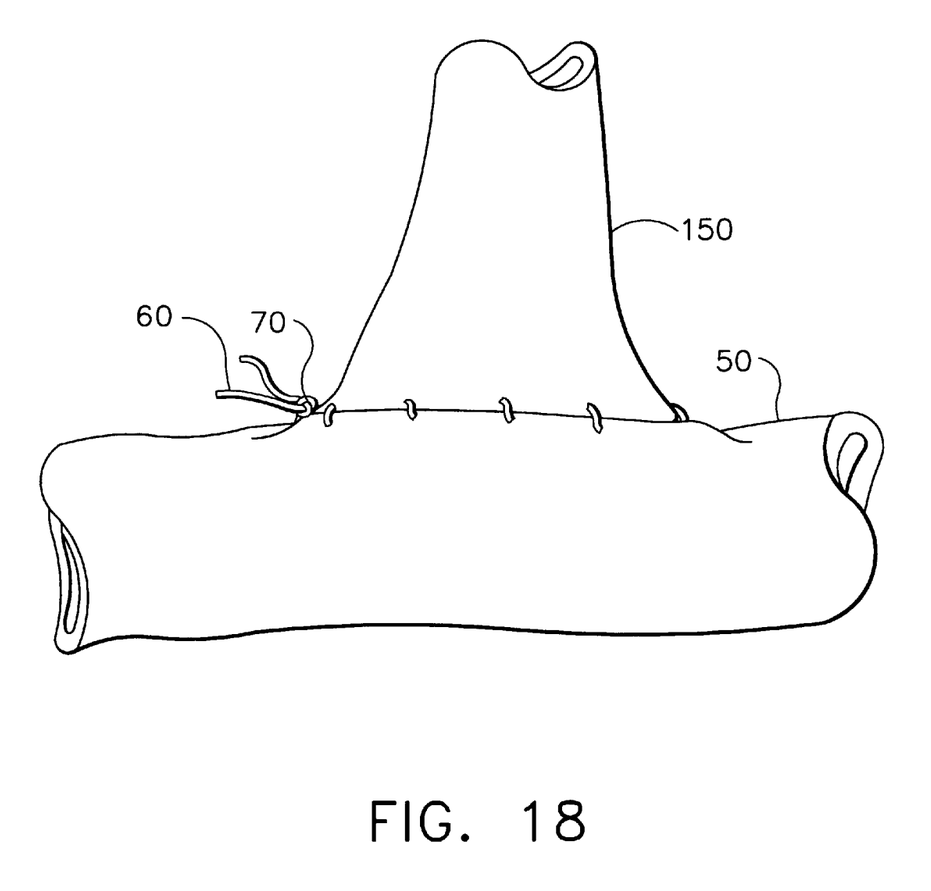
FIG. 18 is a side view of the graft vessel attached to the target vessel by the tightened suture filament, with a surgical knot applied to the free ends of the suture filament, and with the free ends trimmed.

The surgical devices, 110 and 10, are next removed from the blood vessels, 150 and 50, as shown in FIG. 17. The vessels, 50 and 150, are loosely sutured together. By gently pulling on the free ends of the suture filament 60, the vessels are drawn together. A surgical knot is applied next, as shown in FIG. 18, to complete the anastomosis.

While a preferred embodiment of the present invention has been shown and described herein, it will be obvious to those skilled in the art that such an embodiment is provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical device for facilitating the anastomosis of two hollow organs said surgical device comprising:
   a) a handle;
   b) two arms for holding one of the hollow organs, wherein each of said two arms comprises a proximal end attached to said handle and a distal end extending therefrom, each of said two arms further including a holding surface;
   c) a prong interposed between said two arms, said prong having a proximal end attached to said handle, a distal end extending therefrom which is between and substantially unattached to said holding surfaces of said two arms when said two arms are not adjacent to each other; and
   d) a means for moving said distal ends of said two arms adjacent to each other so that said holding surfaces are substantially opposing whereby a hollow organ can be held between said two arms with said prong extending through said hollow organ.

2. The surgical device of claim 1 further including a means for holding said distal ends of said two arms adjacent to each other.

3. The surgical device of claim 2 wherein said means for holding said distal ends of said two arms adjacent to each other comprises each of said two arms having a first and a second bend, said two arms crossing over each other between said first and said second bends, and at least one of said two arms is spring biased to move said distal ends of said arms adjacent to each other.

4. The surgical device of claim 1 further including a gripping means on said holding surface of at least one of said two arms.

5. The surgical device of claim 4 wherein said gripping means comprises a plurality of projections spaced longitudinally on said holding surface of at least one of said two arms.

6. A surgical device for facilitating the anastomosis of two hollow organs, said surgical device comprising:
   a) a handle;
   b) two arms for holding one of the hollow organs, wherein each of said two arms comprises a proximal end attached to said handle and a distal end extending therefrom, and a longitudinal axis extending therebetween;
   b) said two arms further including a holding surface;
   d) said two arms further including a plurality of guides for the placement of surgical fasteners;
   d) a prong interposed between said two arms, said prong having a proximal end attached to said handle, a distal end extending therefrom which is between and substantially unattached to said holding surfaces of said two arms when said two arms are not adjacent to each other, and a longitudinal axis extending therebetween;
   e) a means for moving said distal ends of said two arms adjacent to each other so that said longitudinal axes of said two arms are substantially parallel and said holding surfaces are substantially opposing, whereby a hollow organ is held between said two arms with said prong extending through said hollow organ.

7. The surgical device of claim 6 wherein said guides comprise a plurality of flutes disposed along a top of said arms.

8. The surgical device of claim 6 further including a gripping means on said holding surface of at least one of said two arms.

9. The surgical device of claim 6 wherein said gripping means comprises a plurality of projections spaced longitudinally on said holding surface of at least one of said two arms.

10. The surgical device of claim 6 further including a means for holding said two distal ends of said two arms adjacent to each other.

11. The surgical device of claim 6 wherein said means for holding said two arms adjacent to each other comprises each of said arms having a first and a second bend, said arms crossing over each other between said first and said second bends, and at least one of said two arms spring biased to move said distal ends of said two arms adjacent to each other.

12. A surgical device for facilitating the anastomosis of two hollow organs, said surgical device comprising:
   a) a handle having a proximal and a distal end and a longitudinal axis extending therebetween;
   b) two arms for holding one of the hollow organs, wherein each of said two arms comprises a distal end, a proximal end attached to said distal end of said handle, and a longitudinal axis extending therebetween, said distal ends of said two arms movable adjacent to each other;
   c) said distal end of at least one of said two arms further including a plurality of guides for the placement of surgical fasteners;
   d) said distal end of at least one of said two arms further including a holding surface;
   e) said two arms further including a first and a second bend, each of said arms crossing over the other between said first and said second bends, and at least one of said two arms spring biased to move said distal ends of said arms adjacent to each other, wherein when said two arms are adjacent to each other, said longitudinal axes of said distal ends of said two arms are essentially parallel;
   f) a prong having a proximal end and a distal end with a longitudinal axis extending therebetween, said proximal end of said prong attached to said surgical device, said distal end of said prong for entering a hole of one of said hollow organs, said prong interposed between said two arms such that when said two arms are moved adjacent to each other, said prong and said hollow organ are held between said holding surfaces of said arms, and said longitudinal axis of said prong is essentially parallel to said longitudinal axis of each of said distal ends of said two arms.

13. The surgical device of claim 12 wherein each of said arms has a working surface, wherein said guides comprise a plurality of flutes disposed along said working surface.

14. The surgical device of claim 12 further including a gripping means on said holding surface of at least one of said two arms.

15. The surgical device of claim 12 wherein said gripping means comprises a plurality of projections spaced longitudinally on said holding surface of at least one of said two arms.

16. A method for using a first surgical device in combination with a second surgical device for the anastomosis of a first hollow organ to a second hollow organ comprising:
   a) holding said first hollow organ in a first surgical device according to claim 1;
   b) making a first passage in said first hollow organ while held in said first surgical device;
   c) holding said second hollow organ in a second surgical device according to claim 1;
   d) making a second passage in said second hollow organ while held in said second surgical device;
   e) positioning said first and said second surgical devices adjacent to each other, wherein said first passage of said first hollow organ is near to said second passage of said second hollow organ;
   f) attaching said organs together so that said first and second passages are communicating.

17. The method according to claim 16, wherein said step (f) of attaching said organs together so that said first and second passages are communicating comprises:
   a) making an attachment of a first peripheral edge of said first passage of said first hollow organ to a second peripheral edge of said passage of said second hollow organ, wherein said attachment comprises a suture filament having a needle attached to at least one end, said suture filament being loosely passed through said first and second peripheral edges with the ends of said suture filament extending therefrom;
   b) removing said first and said second surgical devices from said hollow organs;
   c) drawing together said peripheral edges of said first and second passages into contact by tensioning the ends of said suture filament;
   d) tying together with a knot the ends of said suture filament, whereby contact of said first and second passage is maintained for the communication of bodily fluids between said hollow organs.

\* \* \* \* \*